US010292016B2

(12) United States Patent
Kusens

(10) Patent No.: US 10,292,016 B2
(45) Date of Patent: *May 14, 2019

(54) ELECTRONIC IDENTIFICATION, LOCATION TRACKING, COMMUNICATION AND NOTIFICATION SYSTEM WITH BEACON CLUSTERING

(71) Applicant: COLLATERAL OPPORTUNITIES, LLC, Wilmington, DE (US)

(72) Inventor: Michael Kusens, Cooper City, FL (US)

(73) Assignee: COLLATERAL OPPORTUNITIES, LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/825,752

(22) Filed: Nov. 29, 2017

(65) Prior Publication Data
US 2018/0084390 A1    Mar. 22, 2018

Related U.S. Application Data

(63) Continuation of application No. 15/230,415, filed on Aug. 6, 2016, now Pat. No. 9,838,849.
(Continued)

(51) Int. Cl.
*H04W 4/04* (2009.01)
*G01S 1/68* (2006.01)
(Continued)

(52) U.S. Cl.
CPC .............. *H04W 4/043* (2013.01); *G01S 1/68* (2013.01); *G01S 5/14* (2013.01); *G06F 17/3087* (2013.01);
(Continued)

(58) Field of Classification Search
CPC .......... H04W 4/80; H04W 16/28; G06Q 50/12
(Continued)

(56) References Cited

U.S. PATENT DOCUMENTS

| 2003/0146835 | A1* | 8/2003 | Carter ................... G01S 5/0036 340/539.13 |
| 2016/0127875 | A1 | 5/2016 | Zampini, II |

(Continued)

OTHER PUBLICATIONS

Applicant Collateral Opportunities, LLC's pending U.S. Appl. No. 15/845,417, filed Dec. 18, 2017 (currently unpubished).
(Continued)

*Primary Examiner* — Kiet M Doan
(74) *Attorney, Agent, or Firm* — Daniel S. Polley, P.A.

(57) ABSTRACT

A system and method for identifying a customer's location at a business and provide notification to a company representative upon arrival of the customer at the business location. Real-time location determinations for the customer and customer location tracking can be provided. One or more wireless beacons communicate with the customer's electronic device. The beacons provide the system with real-time data about the customer's whereabouts, allowing for the confirmation and tracking of the customer at the location. A first non-limiting example of use, include a company that provides food and beverage allowing the customer to place an order for food and beverages on their electronic device and having the order delivered to the person at their current location as determined by the system. Another non-limiting example includes a company using the notification system to have assigned staff members notified of the customer's arrival.

20 Claims, 15 Drawing Sheets

Sample Hardware Placement

Related U.S. Application Data

(60) Provisional application No. 62/202,357, filed on Aug. 7, 2015.

(51) Int. Cl.

| | |
|---|---|
| *G01S 5/14* | (2006.01) |
| *G06F 17/30* | (2006.01) |
| *G06F 19/00* | (2018.01) |
| *G06Q 50/12* | (2012.01) |
| *H04L 12/24* | (2006.01) |
| *H04W 8/00* | (2009.01) |
| *H04W 8/24* | (2009.01) |
| *H04W 40/24* | (2009.01) |

(52) U.S. Cl.
CPC ........ *G06F 17/30241* (2013.01); *G06F 19/00* (2013.01); *G06F 19/3418* (2013.01); *G06Q 50/12* (2013.01); *H04L 41/0803* (2013.01); *H04W 8/005* (2013.01); *H04W 8/24* (2013.01); *H04W 40/244* (2013.01)

(58) Field of Classification Search
USPC ........ 455/456.3, 456.4, 456.1; 370/311, 328; 340/5.64, 539.13
See application file for complete search history.

(56) References Cited

U.S. PATENT DOCUMENTS

2016/0227359 A1* 8/2016 Hurewitz ................ H04W 4/02
2017/0116651 A1* 4/2017 Greenberger ...... G06Q 30/0281

OTHER PUBLICATIONS

Applicant's Collateral Opportunities, LLC's pending U.S. Appl. No. 15/897,114, filed Feb. 14, 2018 (currently unpublished).
Applicant Collateral Opportunities, LLC's pending U.S. Appl. No. 15/802,594, filed Nov. 3, 2017 (currently unpublished).

* cited by examiner

FIGURE 1: Registration of Customer's Device
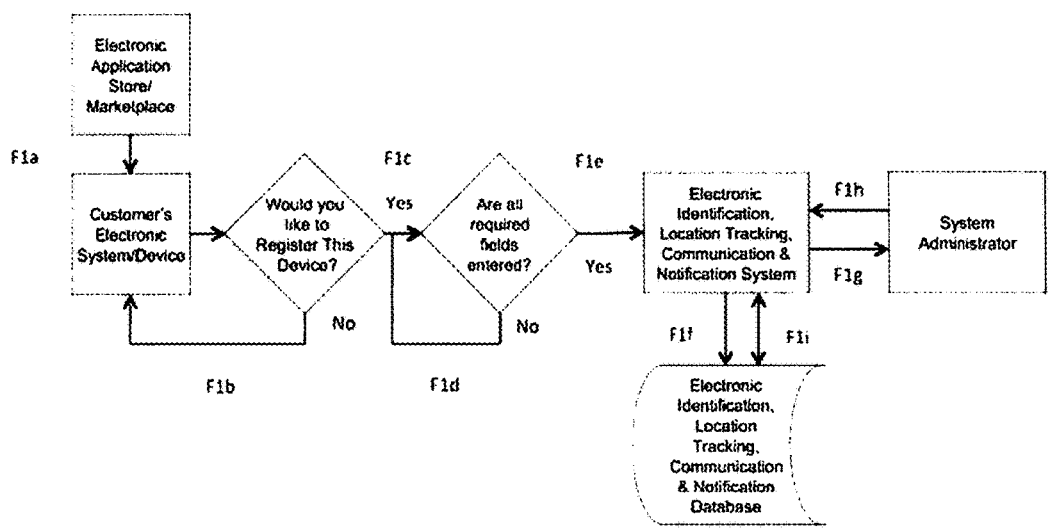
FIGURE 2: Registering a Beacon Location
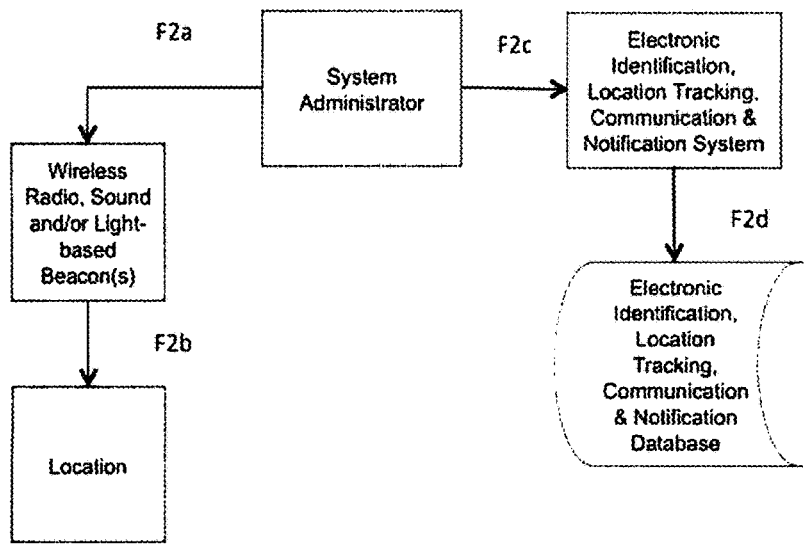

FIGURE 3: Determination of Presence at Location – Embodiment A
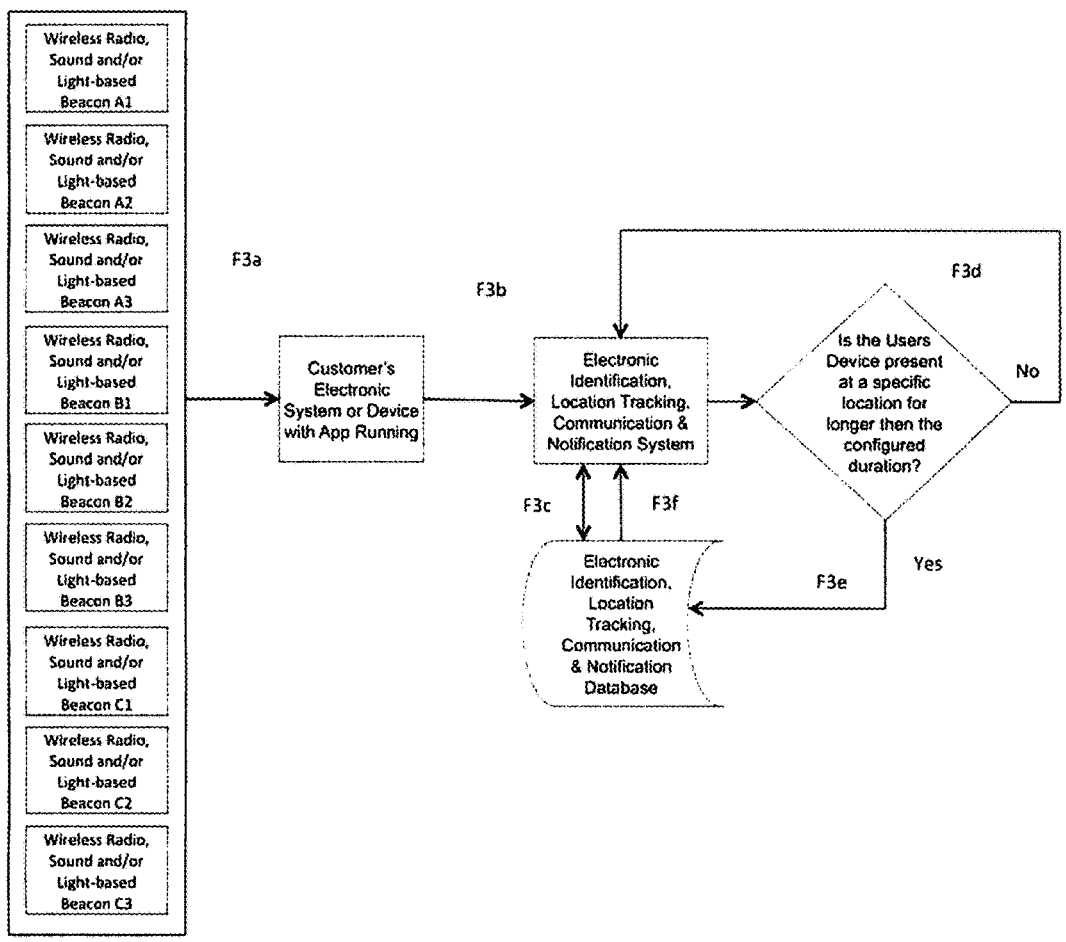

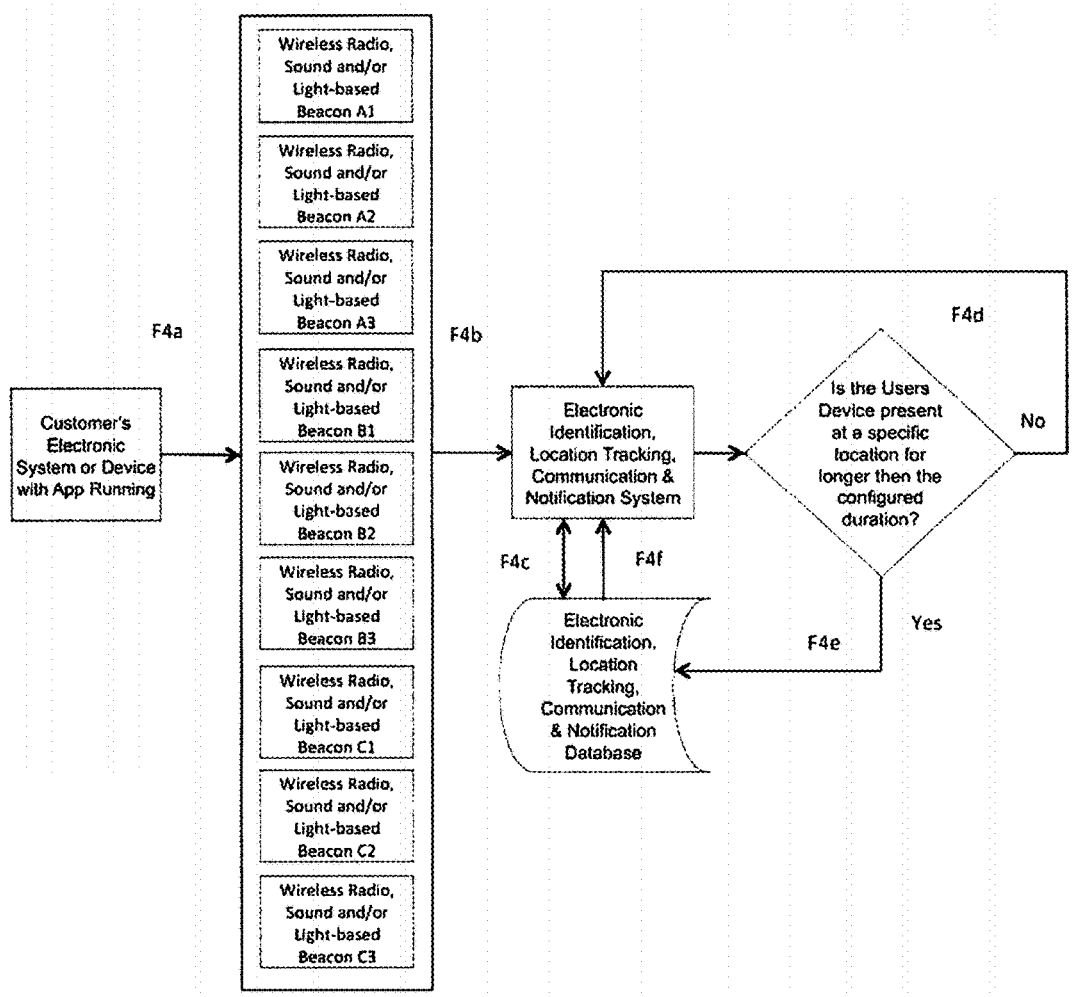
FIGURE 4: Determination of Presence at Location – Embodiment B

FIGURE 5: Notification Rules Engine
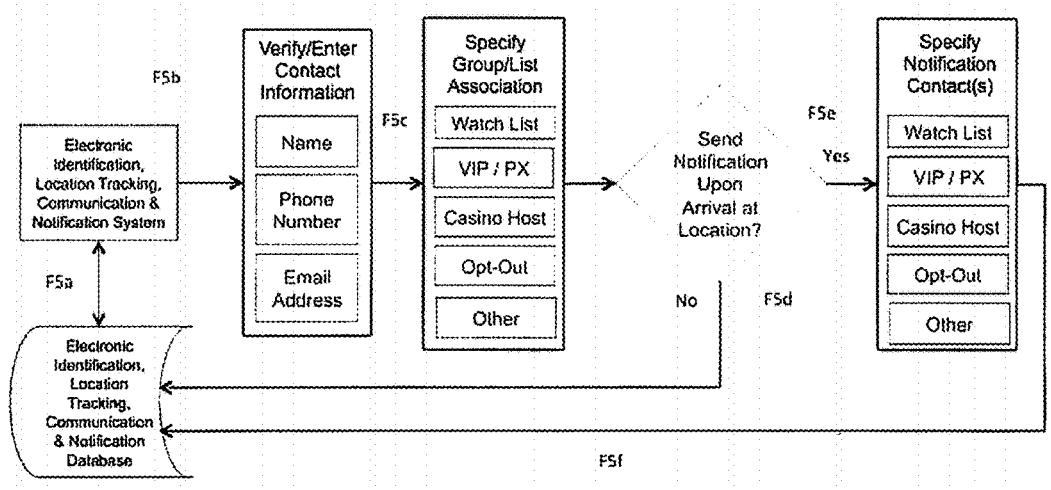

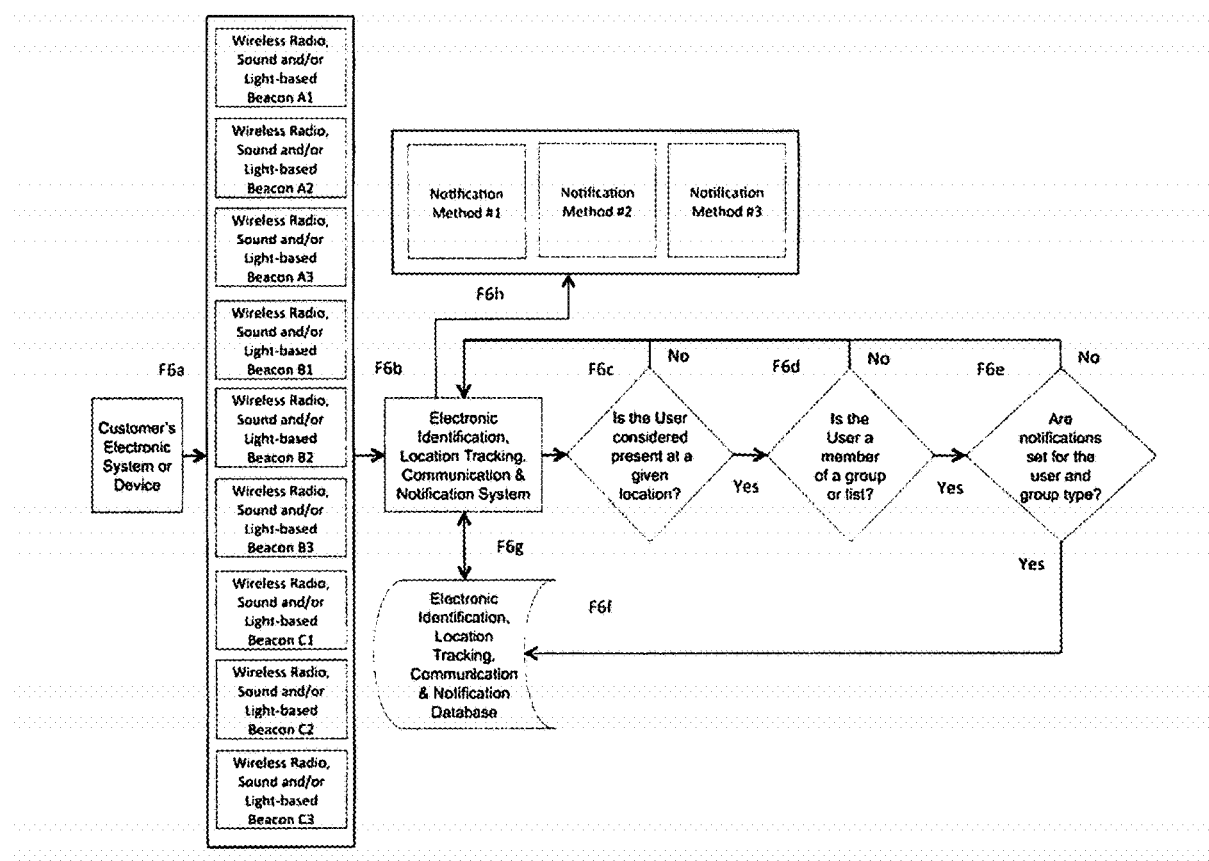
FIGURE 6: Determination and Delivery of Notifications

FIGURE 7: Determination and Delivery of Notifications – Embodiment B
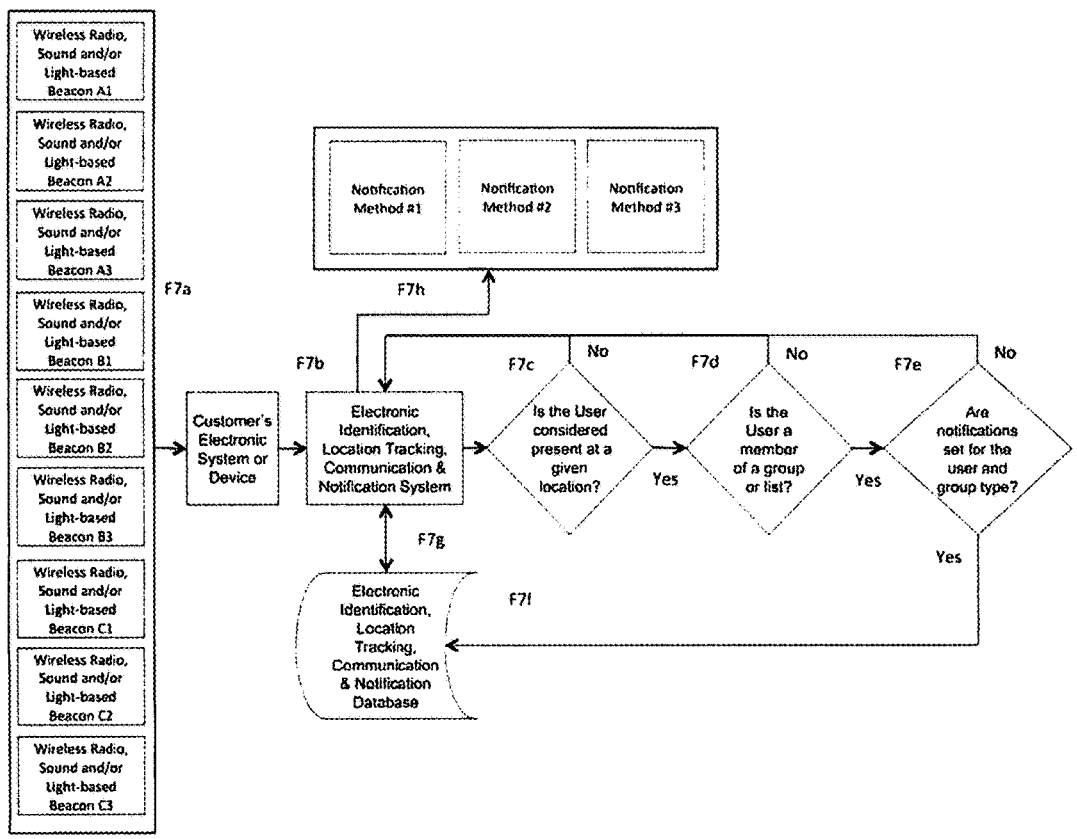

FIGURE 8: Presence Determination at a Location Rules Engine
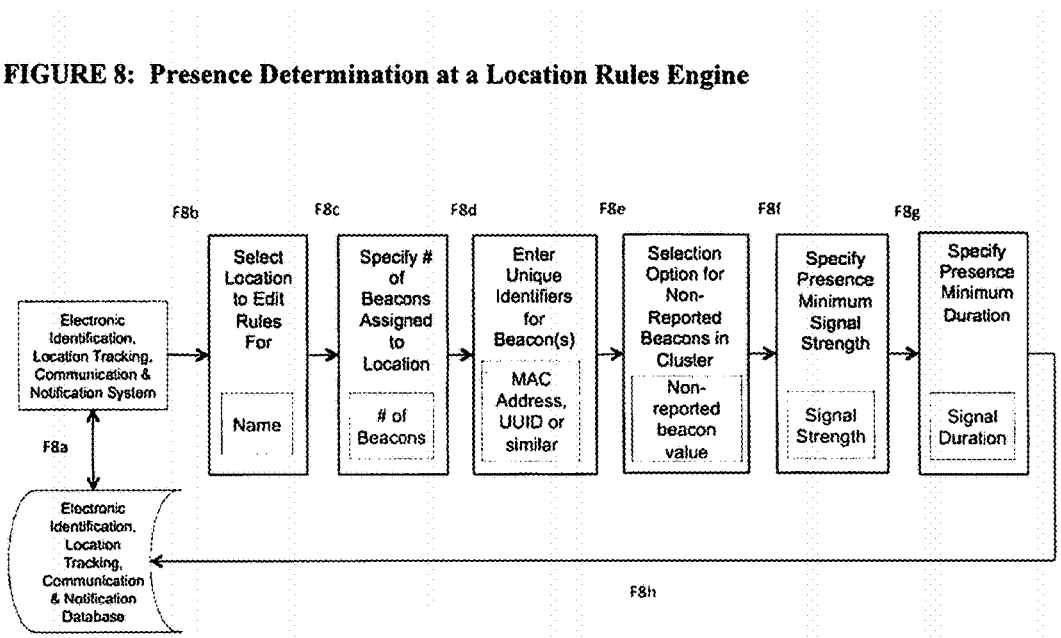
FIGURE 9: Process to Order Goods and/or Services from App
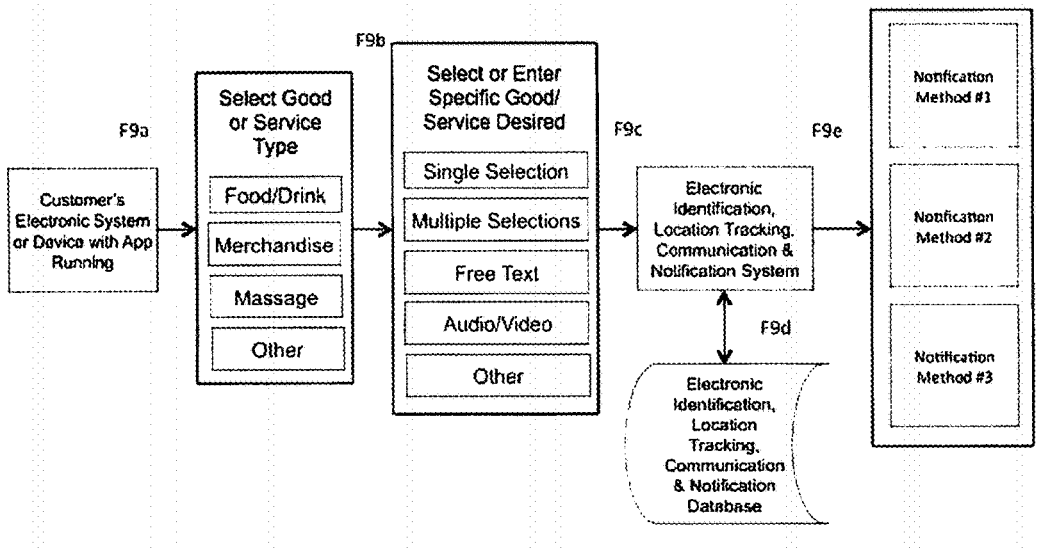

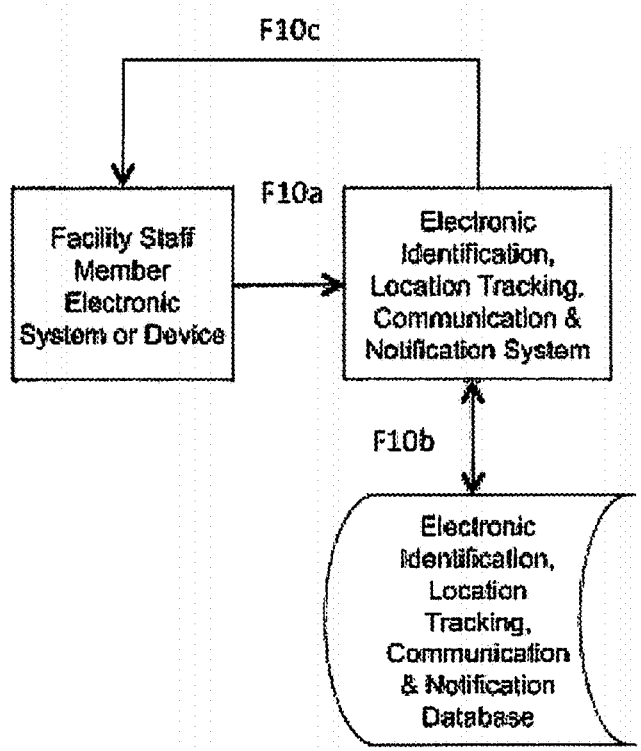
FIGURE 10: Delivery of Good and/or Services to Customers Current Location

FIGURE 11: Customer Opt-Out of Rating/Monitoring by Facility
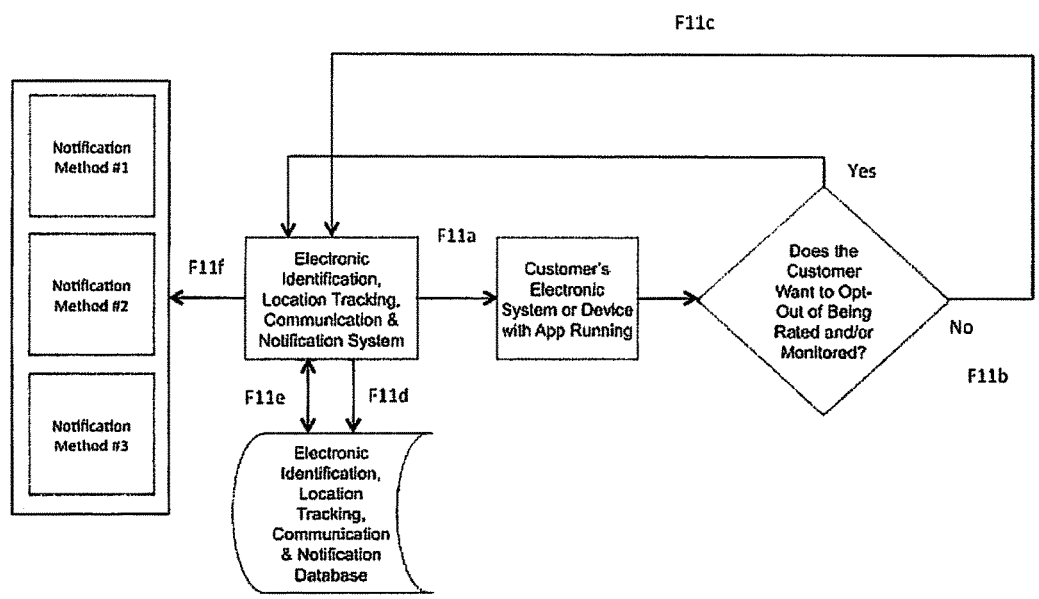

FIGURE 12: Sample of presence determination with Clustering of Beacons in a Location
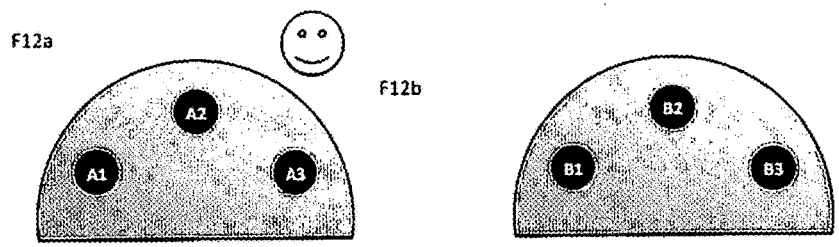
F12a  F12b
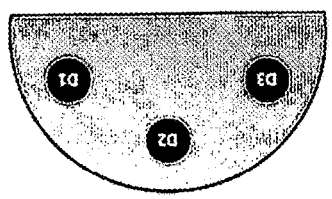 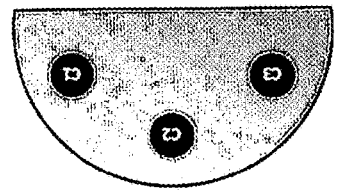
Signal Strength (RSSI, % or other) Data Received
F12c
A1 = 80%    B1 = 82%     C1 = 60%     D1 = 55%
A2 = 85%    B2 = 77%     C2 = 58%     D2 = 57%
A3 = 85%    B3 = 72%     C3 = 55%     D3 = 62%
AVG = 83.33%  AVG = 77.33%  AVG = 57.67%  AVG = 58.00%
F12d    Location = Table A VersaBadge Location Determination for Staff / Visitors VersaBadge Location Determination for Assets Sample Hardware Placement

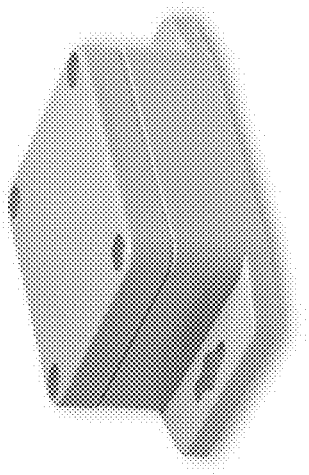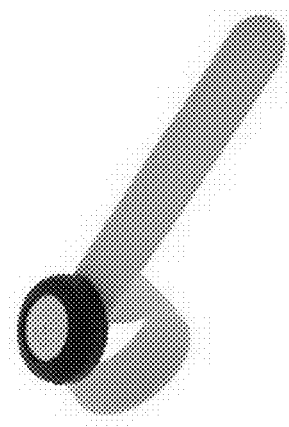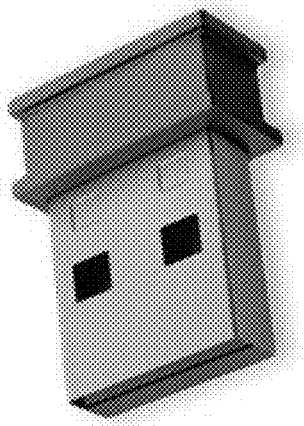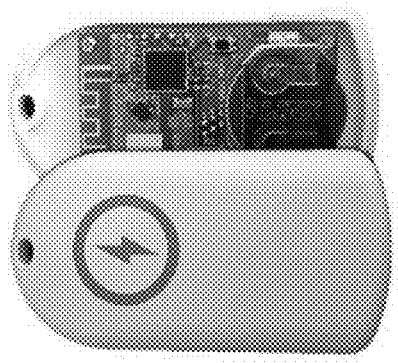
VersaBadge Beacon Options / Form Factors
AA Powered Rugged Beacon
CR2032 Battery Powered Wristband Beacon
USB Powered Beacon
Small CR2032 Battery Powered Beacon
Figure 16

ELECTRONIC IDENTIFICATION, LOCATION TRACKING, COMMUNICATION AND NOTIFICATION SYSTEM WITH BEACON CLUSTERING

This application is a continuation of U.S. patent application Ser. No. 15/230,415, filed Aug. 6, 2016, which claims the benefit of and priority to U.S. Provisional Patent Application Ser. No. 62/202,357, filed Aug. 7, 2015. Both applications are incorporated by reference in their entireties for all purposes.

BACKGROUND

The hospitality industry is highly competitive with companies always looking for competitive advantages, whether it be on price, features or customer service. In recent years, in an effort to differentiate themselves from other competitors, many hospitality companies such as Hotels, Restaurants and Casinos have implemented customer reward and tracking programs. These programs reward customers for a variety of reasons including, but not limited to, spending time at specific locations, spending money at specific locations and/or performing certain activities. Additionally, the reward programs provide a treasure trove of data for the companies on their customers, which assist in marketing efforts, administrative decisions and more.

Current systems require both the customer and company to proactively perform a task in order to be recognized at the location and receive the proper rewards program recognition. Most of the time this is done by the customer handing a card to a company representative and that card information then entered into an existing system. This process is often insufficient for proper tracking of the customer and it is to addressing or reducing these problems that the current disclosure is directed.

SUMMARY OF THE DISCLOSURE

A method and system are described that allow companies (as defined below), to identify a customer's location and provide notification to one or more company representatives upon arrival of the customer at a given location. Additionally, the method and system allow for navigational services to be provided to customers, and real-time location determination, location tracking and confirmation to customers of location and rewards program status.

The disclosed method can be preferably performed through a system of wireless radio, sound and/or light-based beacons communicating with the customer's smartphone, tablet, computer system, or other electronic device. Wireless radio, sound and/or light-based beacons (also collectively referred to as "beacons") provide a system with real-time data about the customer's whereabouts, allowing for the confirmation and tracking described above and below. Depending on the type of location using the system, in certain circumstances one or more functions of the system may not be available to customers and companies alike. As a non-limiting example, where the system is used by a company that provides food and beverage services, a customer can place an order for food/beverages and the order delivered to the person at their current location as determined by the system. As another non-limiting example, a company may choose to implement the notification system to have staff members notified of the arrival of a customer who is assigned to a specific group or list within the system.

The following non-limiting definitions are provided as an aid in understanding at least a preferred embodiment for the disclosed novel method and system:

| Term | Definition |
|---|---|
| Electronic Identification, Location Tracking, Communication & Notification System Database | An electronic database where permissions and locations of guests and members are managed and stored. |
| Electronic Identification, Location Tracking, Communication & Notification System | A specially programmed electronic system which monitors guest and member authorizations and locations based on information received from and being in communication with wireless radio, sound and/or light-based beacons to monitor activity in controlled access areas. |
| Electronic Identification, Location Tracking, Communication & Notification App | A specially designed software application "App" that is installed on the customer's electronic system or device (preferably portable or mobile electronic device) and which allows and directs the customer's electronic system or device to communicate with wireless radio, sound and/or light-based beacons in order to identify the customer's current location. |
| Customer | One or more persons who have entered the physical location of, used by or associated with a company or facility and are patrons of the company's business. |
| Administrator | One or more persons responsible for entering and maintaining information about each customer in the system and/or system database as well as configuring location, notifications and group/list management for the system and/or system database. |
| Facility Staff's Electronic System or Device | A computer system or device (preferably mobile or portable) including, but not limited to, a cell phone, smartphone, key card, tablet, smart watch, laptop or other computer system belonging to a facility that is specially programmed with the Electronic Identification, Location Tracking, Communication & Notification Application and/or which can directly access and communicate with the Electronic Identification, Location Tracking, Communication & Notification System. |
| Customer's Electronic System or Device | A computer system or device (preferably mobile or portable) including, but not limited to, a cell phone, smartphone, key card, tablet, smart watch, laptop or other computer system belonging to a customer that is specially programmed with the Electronic Identification, Location Tracking, Communication & Notification App to permit communication by the Customer's computer system or device with one or more wireless radio, sound and/or light-based beacons. |

| | |
|---|---|
| Wireless Radio, Sound and/or Light-based Beacon | A receiver/transmitter, preferably relatively small, capable of operating on short and/or long range wireless communication between electronic devices. Capabilities include, but are not limited to, pinpointing its own location, being programmed or designed to utilize the software in a smart phone, cellular phone, smart watch, or other electronic device to determine that device's location and bi-directional data transmission. Wireless radio, sound and/or light-based beacons can utilize technologies including, but not limited to, Near Field Communication (NFC), Bluetooth, WiFi, Light-Fidelity (LiFi), Ultrasound, InfraRed (IR), and Radio Frequency (RF). All of these technologies and similar current or similar later developed communication technologies are included in the term "wireless radio" wherever that term appears in this disclosure. |
| Device | A smartphone, cellular phone, computer, tablet, smart watch, laptop or any electronic device (preferably portable or mobile) with wireless radio, sound and/or light-based beacon capability and specifically programmed with the below defined "Permissions Application". |
| Location Cluster | A group of Wireless Radio, Sound and/or Light-based Beacons which as a group are utilized in connection with all members of the group in the determination of a customer's location. |

BRIEF DESCRIPTION OF THE DRAWINGS

FIG. 1 is a process flow and block diagram illustrating the registration of a customer's device in accordance with one embodiment for the disclosed system and method;

FIG. 2 is a process flow and block diagram illustrating the registration of a beacon location in accordance with one embodiment for the disclosed system and method;

FIG. 3 is a process flow and block diagram illustrating a first embodiment for determining a customer's presence at location by the disclosed system and method;

FIG. 4 is a process flow and block diagram illustrating a second embodiment for determining a customer's presence at location by the disclosed system and method;

FIG. 5 is a process flow and block diagram of a notification rules engine in accordance with one embodiment for the disclosed system and method;

FIG. 6 is a process flow and block diagram illustrating a first embodiment for the determination and delivery of notifications in accordance with one embodiment for the disclosed system and method;

FIG. 7 is a process flow and block diagram illustrating a second embodiment for the determination and delivery of notifications in accordance with one embodiment for the disclosed system and method;

FIG. 8 is a process flow and block diagram illustrating a customer's presence at a location determination rules engine in accordance with one embodiment for the disclosed system and method;

FIG. 9 is a process flow and block diagram illustrating the ordering of goods and/or services in accordance with one embodiment for the disclosed system and method;

FIG. 10 is a process flow and block diagram illustrating the delivery of goods and/or services to a customer's current location in accordance with one embodiment for the disclosed system and method;

FIG. 11 is a process flow and block diagram illustrating a customer opt-out of rating/monitoring by a company in accordance with one embodiment for the disclosed system and method;

FIG. 12 illustrates a sample of a customer presence determination using beacon clustering at a location in accordance with one embodiment for the disclosed system and method;

FIG. 16 illustrates several non-limiting examples for beacons that can be used with the disclosed system and method;

DESCRIPTION OF THE DRAWINGS

Figure 13:
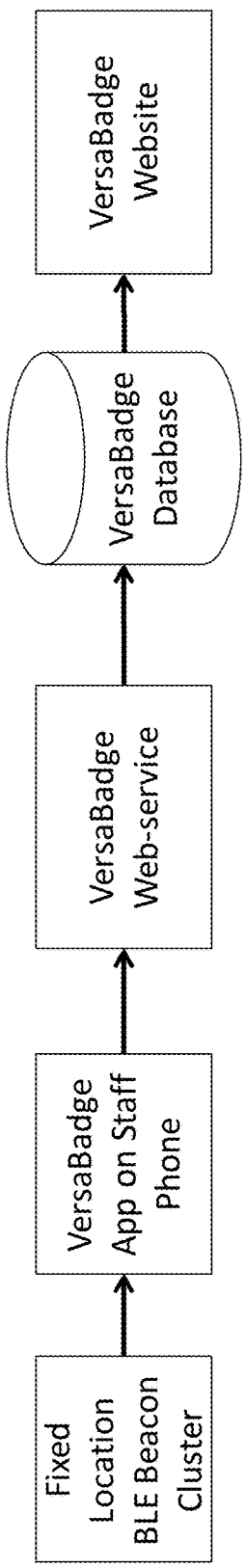
FIG. 13 is a process flow and block diagram for system determinations for staff and/or visitors.
Figure 14:
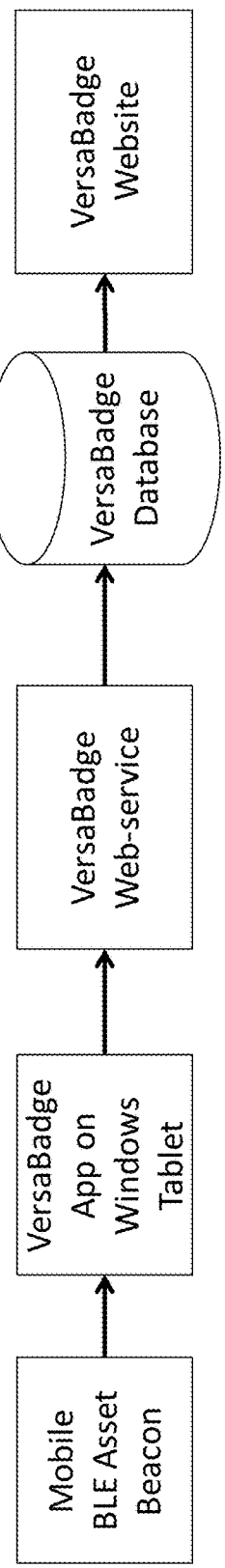
FIG. 14 is a process flow and block diagram for system determinations for assets.
Figure 15:
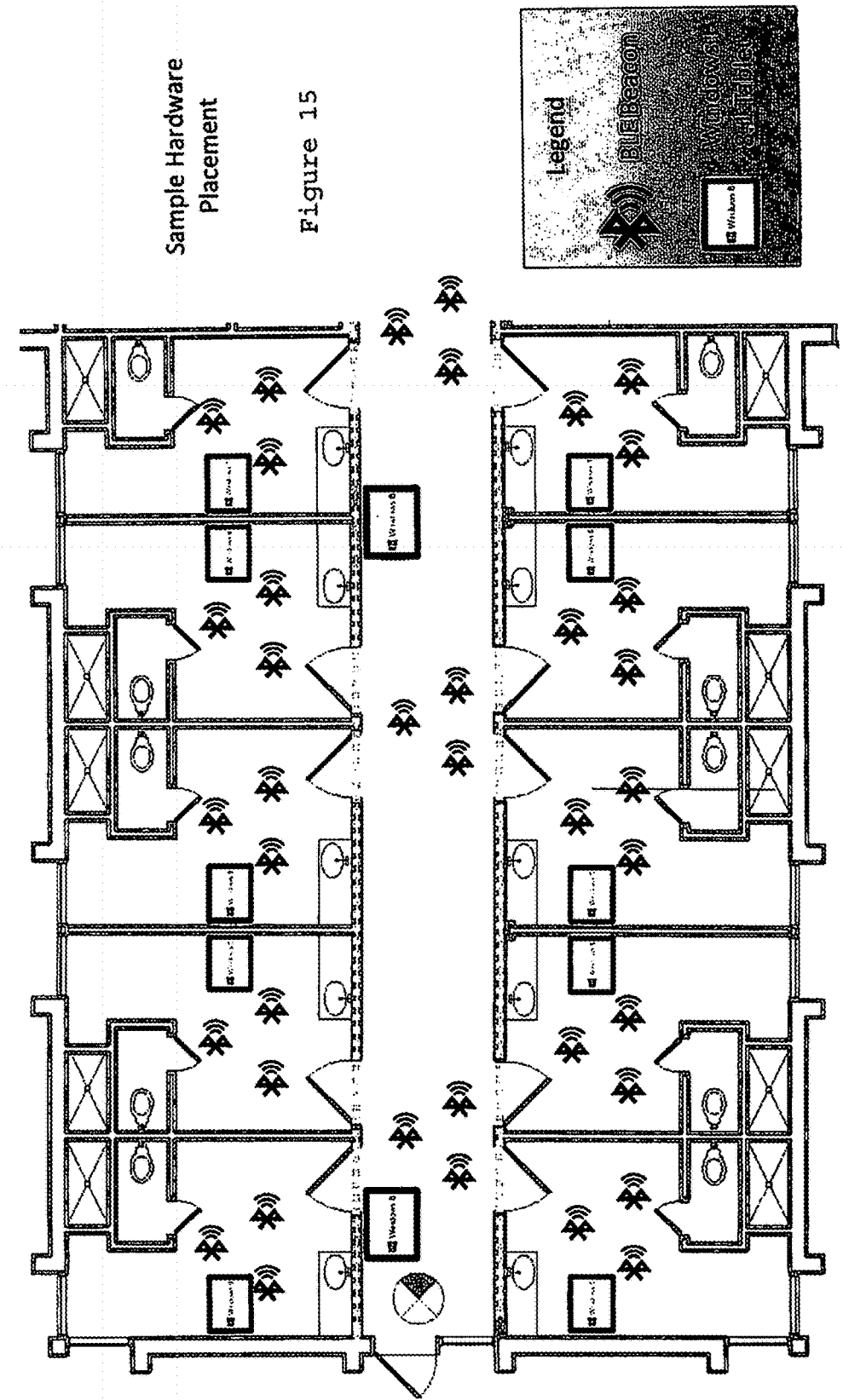
FIG. 15 is a sample hardware (beacons and electronic devices/tablets) placement illustrating for a location.

FIG. 1 shows one method for allowing a customer to register their computer system or device with the electronic identification, location tracking, communication and notification system of a particular company or business. Without limitation, this initial process allows a customer to be electronically and automatically tracked within the company's location, receive rewards program credits, order services delivered to their location and communicate with company employees.

At F1a, a customer downloads and installs the Electronic Identification, Location Tracking, Communication & Notification Application "App" from their computer or any app store or marketplace including, but not limited to, the Apple App Store, Windows Store and Google Play marketplace. The App is downloaded to the customer's electronic system or device. The App can also be preloaded on the Customer's electronic device at the time the customer purchases or otherwise receives the electronic device.

At F1b, when the App is first opened, it preferably prompts the user/customer to register their electronic computer system or device with the electronic identification, location tracking, communication and notification system. This enables the customer to use their computer system or device to be automatically tracked within the customer's facility, communicate with the company, order food, beverage or other products/services, etc. Where the customer is interested in ordering food, beverage and/or other products or services, a menu or listing of the food, beverage and other products/services offered at the location can be displayed on the customer's electronic system or device to inform the customer of what is available at the location. If the user opens the App and does not wish to register the device, then the App can be programmed to operate in a non-registered mode that can limit the services available to the user/customer on the device.

At F1c, if the customer would like to register the device with the electronic identification, location tracking, communication and notification system, a form can appear on the screen prompting the customer for information including, but not limited to, one or more of the following: their name, birthday, mailing address, email address, phone number and picture. The system and software can also be designed such that multiple electronic systems and devices are associated with one account so that the rewards given to each electronic system or device are accumulated within one account (i.e. smartphones of a husband and wife and their children associated with one account so that all points or rewards earned based on activities of the family are accumulated into one account). The required fields can be selected by the company and can depend on the specific company and needs of that company. The customer electronically submits/transmits the form when completed.

At F1d, if during submission by the customer, the App determines that not all required fields are filled out, it will prompt the customer for the missing information. The user can resubmit the form with the missing information provided.

At F1e, once all required fields are provided and the form is submitted by the customer, the data is sent to the electronic identification, location tracking, communication and notification system for processing.

At F1f, the electronic identification, location tracking, communication and notification system electronically stores the customers form submissions along with some identifying information for the customer's device such as, but not limited to, one or more of the following: the device name, UUID, MAC address, IP Address, or other unique identifiers for the customer's device. The information submitted by the customer and the customer's device's identifying information can all be electronically stored in the electronic identification, location tracking, communication and notification database.

At F1g, an electronic notification can be sent to the system administrator(s) via email, sms, mms, voice, fax or other electronic method of the new customer registration.

At F1h, the system administrator can access the electronic identification, location tracking, communication and notification system to view and edit/update the new customer's profile. The system administrator can assign the customer to any group or list available, create notification rules for the customer or add information about the customer in its profile.

At F1i, the system administrator's edits/updates to the customer's profile can be stored in the electronic identification, location tracking, communication and notification database.

FIG. 2 illustrates a preferred embodiment for how a location is registered with the electronic identification, location tracking, communication and notification system.

At F2a, a system administrator configures either a single or cluster of wireless radio, sound and/or light-based beacon(s) with information including, but not limited to, one or more of the following its name, unique identifier (MAC Address, UUID or similar), group/organization, unique number within an organization, location, wireless networks, etc. A cluster of beacons is created when two or more beacons are grouped together to define a single location. The system administrator can select various options with regards to what the system should do when it does not receive a signal from a beacon assigned to a given location cluster. Options include, but are not limited to, discarding the particular location from a presence determination if a signal from one or more of the beacons configured for the cluster associated with the particular location is not received, assigning a default or static value for the beacon signal strength for any beacon that is assigned to the particular cluster that didn't send a signal or a signal of sufficient strength (threshold), or ignoring the beacon from consideration in the presence determination. Location determination for a cluster of beacons can based on an average of the signal strength received by a device and/or system from all of the beacons assigned to a given cluster of a location and subject to the option specified above.

Preferably, the clustering method can be designed to enable micro-location services (i.e. be able to provide accurate location at a sub-room level). In one non-limiting example, the distances of the clusters can preferably range from about a few feet radius to about a 15 feet radius. The beacons for the cluster can be placed anywhere from right next to each other up to a few feet apart, depending on the level of accuracy needed for the given use. In the casino world, a non-limiting example can be three beacons at each blackjack/card table to form the cluster for that table. Clusters can be defined from a logical perspective as a specific location (i.e. Blackjack Table 1, Blackjack Table 2, etc.). From a technical perspective, the beacon clusters can be defined by using their UUID, Major and Minor values (identifiers). All beacons in a cluster preferably has the same UUID and Major value with each one having a unique minor value.

At F2b, the configured wireless radio, sound and/or light-based beacon(s) are physically installed at the configured/assigned location(s) and tested to ensure its (their) operability.

At F2c, a system administrator then electronically accesses the electronic identification, location tracking, communication and notification system to enter in the installed wireless radio, sound and/or light-based beacon(s)' configuration and location information. Alternatively, this information can be electronically received from the beacon signals and electronically downloaded by the system. Beacon clusters can be defined at this point as well. When a location is created, the user inputs the number of beacons used to define that specific location. When a cluster of beacons is configured for a location, the system preferably uses the average of the received signal strengths for all beacons in a cluster in determining location or presence at a location. As a non-limiting example, if a location is configured for a cluster of 3 beacons, the signal strength received from each of the beacons is averaged to create a single location signal strength value. Optionally, should a beacon signal not be received for any given beacon assigned to a location cluster, the system can either assign a dummy value for this particular beacon signal, choose to ignore all beacons for this location or only calculate the average based on the beacons who did provide a signal. Additional configuration of the beacon(s) can also be performed at this step, which can include, but is not limited to, configuring notification settings, signal types, signal strengths, transmission power and device presence durations.

At F2d, the wireless radio, sound and/or light-based beacon's configuration and location information can be stored in the electronic identification, location tracking, communication and notification database.

FIG. 3 illustrates one embodiment of how the system determines the location of a customer based on their registered device.

At F3a, the wireless radio, sound and/or light-based beacons installed at various locations are constantly and automatically broadcasting their information including, but not limited to, one or more of the following: its name, unique identifier (MAC Address, UUID or similar), group/organization, unique number within an organization, location, wireless networks, etc.

At F3b, the customer's electronic system or device with the Electronic Identification, Location Tracking, Communication & Notification Application "App" downloaded and running (either in the foreground or as a background service) receives the broadcasted information from the wireless radio, sound and/or light-based beacons and transmits the information received, along with additional information including, but not limited to, one or more of the following: the customer's or the customer's device's name, unique identifier (MAC Address, UUID or similar), group/organization, signal type and strength to the Electronic Identification, Location Tracking, Communication & Notification system. This process repeats at configurable intervals so that the App can be frequently transmitting beacon information to the Electronic Identification, Location Tracking, Communication & Notification System.

At F3c, the Electronic Identification, Location Tracking, Communication & Notification System queries the Electronic Identification, Location Tracking, Communication & Notification Database to determine the location and other settings configured in F2c for each of the configured beacons information sent by the App on the customer's device.

At F3d, the Electronic Identification, Location Tracking, Communication & Notification System analyzes the data received from the App and compares it against the retrieved configuration settings (See FIG. 8) for each wireless radio, sound and/or light-based beacon location it received information from. If the customer's device is not considered present at a location based on the analysis of the Electronic Identification, Location Tracking, Communication & Notification System, it will continue to check the next data set received from the App and repeat this step. As a non-limiting example, the signal strength, which in this instance can be measured and calculated on a scale of 0 to 100% can be configured to a minimum threshold of 80% as in F8c. This means that unless the customer's device receives a signal from the wireless radio, sound and/or light-based beacons greater then the 80% strength threshold, they cannot be considered present at a location. Additionally, a minimum signal strength duration value may be specified for a given location as in F8d. If so configured, once the App on a customer's electronic system or device reports a signal strength value above the minimum threshold, it preferably must also continue to report a signal strength value above that minimum threshold for the configured duration threshold in order to be considered present at that location. Continuing from the example above, if this minimum duration threshold is set to 20 seconds, the App must continue to report a signal strength value above the 80% value for a duration of 20 consecutive seconds in order to consider the customer's electronic system or device present at that location. Signal strength can be measured in terms of decibels or rssi. For decibels, the receiving device (phone, tablet, etc) can simply measure the signal strength in db. Also, a fixed value can be configured for the transmit power strength of the beacons and that power level (in db) can be used in the calculation of the RSSI (relative signal strength indicator) which is an industry standard measurement algorithm that factors in the received signal strength in Db and compares it against the known transmit power.

At F3e, if the analysis performed in F3d indicates that the customer's device is present at a given location, the status of that customer's device is updated with that location(s) information. The location determinations can also be stored in the Electronic Identification, Location Tracking, Communication & Notification database.

At F3f, the Electronic Identification, Location Tracking, Communication & Notification Database prompts or provides information to the Electronic Identification, Location Tracking, Communication & Notification System of the location confirmation so that any notification rules specified for that location and/or customer can be executed by the system.

FIG. 4 illustrates a different embodiment of how the system determines the location of customer based on their registered device.

At F4a, the customer's electronic system or device with the Electronic Identification, Location Tracking, Communication & Notification Application "App" downloaded and running is preferably constantly and automatically broadcasting it's information including, but not limited to, one or more of the following the customer or customer's device' name, unique identifier (MAC Address, UUID or similar), group/organization, unique number within an organization, location, wireless networks, etc.

At F4b, the wireless radio, sound and/or light-based beacons installed at various locations receive the broadcasted information from the App on the customer's device and transmits the information received, along with additional information including, but not limited to, one or more of the following the beacon's name, unique identifier (MAC Address, UUID or similar), group/organization, signal type and strength to the Electronic Identification, Location Tracking, Communication & Notification system. This process repeats at configurable intervals so that the App can be frequently transmitting beacon information to the Electronic Identification, Location Tracking, Communication & Notification System.

At F4c, the Electronic Identification, Location Tracking, Communication & Notification System queries the Electronic Identification, Location Tracking, Communication & Notification Database to determine the location and other settings configured in F2c for each of the beacons information sent by the App on the customer's device.

At F4d, the Electronic Identification, Location Tracking, Communication & Notification System analyzes the data received from the App and compares it against the retrieved configuration settings (See FIG. 8) for each wireless radio, sound and/or light-based beacon location it received information from. If the customer's device is not considered present at a location based on the analysis of the Electronic Identification, Location Tracking, Communication & Notification System, it will continue to check the next data set received from the App and repeat this step. As a non-limiting example, the signal strength, which in this instance can be measured and calculated on a scale of 0 to 100% can be configured to a minimum threshold of 80% as in F8c. This means that unless the customer's device receives a signal from the wireless radio, sound and/or light-based beacons greater then the 80% strength threshold, they cannot be considered present at a location. Additionally, a minimum signal strength duration value may be specified for a given location as in F8d. If so configured, once the App on a customer's electronic system or device reports a signal strength value above the minimum threshold, it must continue to report a signal strength value above that minimum threshold for the configured duration threshold in order to be considered present at that location. Continuing from the example above, if this minimum duration threshold is set to 20 seconds, the App must continue to report a signal strength value above the 80% value for a duration of 20 consecutive seconds in order to consider the customer's electronic system or device present at that location.

At F4e, if the analysis performed in F4d indicates that the customer's device is present at a given location, the status of that customer's device is updated with that location(s) information. The location determinations can also be stored in the Electronic Identification, Location Tracking, Communication & Notification database.

At F4f, the Electronic Identification, Location Tracking, Communication & Notification Database prompts or provides information to the Electronic Identification, Location Tracking, Communication & Notification System of the location confirmation so that any notification rules specified for that location and/or customer can be executed.

FIG. 5 demonstrates a non-limiting preferred embodiment for how notifications can be configured within the Electronic Identification, Location Tracking, Communication & Notification System. This process can also be utilized to edit profile information and notifications for existing customers.

At F5a, the Electronic Identification, Location Tracking, Communication & Notification System queries the Electronic Identification, Location Tracking, Communication & Notification Database for the desired customer's existing information. This function can be typically reserved for a system administrator.

At F5b, the Electronic Identification, Location Tracking, Communication & Notification System can display the retrieved customer's profile information and verifies the accuracy of the information. The system administrator may also enter new and/or updated information in the customer's profile if so desired.

At F5c, once the customer's profile information is verified and/or updated (where a verification or updating step is performed), the system administrator may add the customer to one or more groups or lists maintained within the system. The system may also allow for default groups/lists to be assigned to all customers of a facility.

At F5d, once the groups and/or lists are selected, the system administrator has the option of sending notifications upon confirmation of their presence as described in FIGS. 3 and/or 4, at any location configured in the Electronic Identification, Location Tracking, Communication & Notification System. If no notifications are desired, the customer's profile information is updated in the Electronic Identification, Location Tracking, Communication & Notification Database.

At F5e, if the system administrator desired to configure notifications for the customer they will now configure the notification recipient(s) and type of notification to be sent upon confirmation of their presence as described in FIGS. 3 and/or 4, at any location configured in the Electronic Identification, Location Tracking, Communication & Notification System. More than one notification can be configured for a given customer.

At F5f, the customer's profile information is updated in the Electronic Identification, Location Tracking, Communication & Notification Database along with the configured notification settings.

FIG. 6 demonstrates how the system determines if a notification is to be delivered, where the notification is to be delivered and how the notification is to be delivered.

At F6a, the customer's electronic system or device with the Electronic Identification, Location Tracking, Communication & Notification Application "App" downloaded and running (either in the foreground or as a background service) can be constantly and automatically broadcasting it's information including, but not limited to, one or more of the following the customer's and/or customer's device's name, unique identifier (MAC Address, UUID or similar), group/organization, unique number within an organization, location, wireless networks, etc.

At F6b, the wireless radio, sound and/or light-based beacons installed at various locations receive the broadcasted information from the App on the customer's device and transmit the information received, along with additional information including, but not limited to, signal type and strength to the Electronic Identification, Location Tracking, Communication & Notification system. This process repeats at configurable intervals so that the beacons are frequently transmitting and automatically customer device information to the Electronic Identification, Location Tracking, Communication & Notification System. In the embodiment shown in FIG. 6, the phone can perform the broadcasting of its identifiers which can be the exact same type of identifiers as in other figures and the beacons can act as receivers for that signal. The notification determinations and delivery shown in FIG. 7 and discussed below, can work similar to F3b in FIG. 3, while FIG. 6 shows how the system can be used in a different manner.

At F6c, the Electronic Identification, Location Tracking, Communication & Notification System queries the Electronic Identification, Location Tracking, Communication & Notification Database in order to receive information to allow it to determine the settings configured in F2c for each of the beacons sent information by the App on the customer's device.

At F6d, the Electronic Identification, Location Tracking, Communication & Notification System analyzes the data received from the App and compares it against the retrieved configuration settings (See FIG. 8) for each wireless radio, sound and/or light-based beacon location it received information from. If the customer's device is not considered present at a location based on the analysis of the Electronic Identification, Location Tracking, Communication & Notification System, it will continue to check the next data set received from the App and repeat this step. As a non-limiting example, the signal strength, which in this instance can be measured and calculated on a scale of 0 to 100% was configured to a minimum threshold of 80% as in F8c. This means that unless the customer's device receives a signal from the wireless radio, sound and/or light-based beacons greater then the 80% strength threshold, they cannot be considered present at a location. Additionally, a minimum signal strength duration value may be specified for a given location as in F8d. If so configured, once the App on a customer's electronic system or device reports a signal strength value above the minimum threshold, it must continue to report a signal strength value above that minimum threshold for the configured duration threshold in order to be considered present at that location. Continuing from the example above, if this minimum duration threshold is set to 20 seconds, the App must continue to report a signal strength value above the 80% value for a duration of 20 consecutive seconds in order to consider the customer's electronic system or device present at that location.

At F6e, if the analysis performed in F6d indicates that the customer's device is present at a given location, the system determines if the user is a member of a group or list. If the user is not a member of a group or list, no notifications related to the group or list are sent and the status of that customer's device is updated with that locations information. However, other non-group or list related notifications (i.e. drink specials, gift shop discounts, etc.) can be set electronically sent to the customer's device.

At F6f, if the customer is determined to be a member of a group or list based on the analysis performed in F6e, the system next determines what, if any, notifications are configured for the group or list. If notifications are not configured for the group or list the customer is assigned to, no notifications are sent and the status of that customer's device is updated with that locations information. However, other non-group or list related notifications (i.e. drink specials, gift shop discounts, etc.) can be set electronically sent to the customer's device.

At F6g. if notifications are configured for the user based on the analysis in F6f, the Electronic Identification, Location Tracking, Communication & Notification Database is updated so the notifications can be queued up.

At F6h, the Electronic Identification, Location Tracking, Communication & Notification Database prompts the Electronic Identification, Location Tracking, Communication & Notification System to send out the configured notifications.

At F6i, notifications are sent out by the Electronic Identification, Location Tracking, Communication & Notification System via any of the available and configured methods. These methods include, but are not limited to, one or more of the following: Email, SMS, MMS, On Screen and Voice. The notifications are designed to inform specific staff members or departments of the facility when specific customers arrive at the location. One non-limiting example of a notification can be a SMS message sent to a Host that one of their VIP customers arrives at the facility. Another non-limiting example notification can be a popup window on a computer screen for the security department when someone tagged on a Watch List arrives at the facility. By having the novel system described herein installed, a company or organization can have staff members or management be notified when certain classes of customers or specific customers arrive at their place of business.

FIG. 7 demonstrates another embodiment of how the system determines if a notification is to be delivered, where the notification is to be delivered and how the notification is to be delivered.

At F7a, the wireless radio, sound and/or light-based beacons installed at various locations are constantly and automatically broadcasting information including, but not limited to, its name, unique identifier (MAC Address, UUID or similar), group/organization, unique number within an organization, location, wireless networks, etc.

At F7b, the customer's electronic system or device with the Electronic Identification, Location Tracking, Communication & Notification Application "App" downloaded and running (either in the foreground or as a background service) receives the broadcasted information from the wireless radio, sound and/or light-based beacons and transmits the information received, along with additional information including, but not limited to, one or more of the following: the customer's name and/or the customer's device's name, unique identifier (MAC Address, UUID or similar), group/organization, unique number within an organization, signal type and strength to the Electronic Identification, Location Tracking, Communication & Notification system. This process repeats at configurable intervals so that the customer's device is frequently transmitting beacon information to the Electronic Identification, Location Tracking, Communication & Notification System.

Thus, as evident by the above Figures, the system can be designed such that sometimes the beacons communicate with the system and other times the customer's electronic device communicates with the system.

At F7c, the Electronic Identification, Location Tracking, Communication & Notification System queries the Electronic Identification, Location Tracking, Communication & Notification Database to determine the settings configured in F2c for each of the locations and/or beacons information sent by the App on the customer's device.

At F7d, the Electronic Identification, Location Tracking, Communication & Notification System analyzes the data received from the App and compares it against the retrieved configuration settings (See FIG. 8) for each wireless radio, sound and/or light-based beacon location it received information from. If the customer's device is not considered present at a location based on the analysis of the Electronic Identification, Location Tracking, Communication & Notification System, it will continue to check the next data set received from the App and repeat this step. As a non-limiting example, the signal strength, which in this instance can be measured and calculated on a scale of 0 to 100% was configured to a minimum threshold of 80% as in F8c. This means that unless the customer's device receives a signal from the wireless radio, sound and/or light-based beacons greater then the 80% strength threshold, they cannot be considered present at a location. Additionally, a minimum signal strength duration value may be specified for a given location as in F8d. If so configured, once the App on a customer's electronic system or device reports a signal strength value above the minimum threshold, it must continue to report a signal strength value above that minimum threshold for the configured duration threshold in order to be considered present at that location. Continuing from the example above, if this minimum duration threshold is set to 20 seconds, the App must continue to report a signal strength value above the 80% value for a duration of 20 consecutive seconds in order to consider the customer's electronic system or device present at that location.

At F7e, if the analysis performed in F7d indicates that the customer's device is present at a given location, the system determines if the user is a member of a group or list. If the user is not a member of a group or list, no notifications related to the group or list are sent and the status of that customer's device is updated with that locations information. However, other non-group or list related notifications (i.e. drink specials, gift shop discounts, etc.) can be set electronically sent to the customer's device.

At F7f, if the customer is determined to be a member of a group or list based on the analysis performed in F7e, the system next determines what, if any, notifications are configured for the group or list. If notifications are not configured for the group or list the customer is assigned to, no notifications are sent and the status of that customer's device is updated with that locations information. However, other non-group or list related notifications (i.e. drink specials, gift shop discounts, etc.) can be set electronically sent to the customer's device.

At F7g, if notifications are configured for the user based on the analysis in F7f, the Electronic Identification, Location Tracking, Communication & Notification Database is updated so the notifications can be queued up.

At F7h, based on information stored in the Electronic Identification, Location Tracking, Communication & Notification Database the Electronic Identification, Location Tracking, Communication & Notification System is prompted to send out the configured notifications.

At F7i, notifications are sent out by the Electronic Identification, Location Tracking, Communication & Notification System via any of the available and configured methods. These methods include, but are not limited to, Email, SMS, MMS, On Screen and Voice. The notifications are designed to inform specific staff members or departments of the facility when specific customers arrive at the location. One non-limiting example of a notification can be a SMS message sent to a Host that one of their VIP customers arrives at the facility. Another non-limiting example notification is a popup window on a computer screen for the security department when someone tagged on a Watch List arrives at the facility.

FIG. 8 demonstrates how a customer's presence at a location is determined and configured within the Electronic Identification, Location Tracking, Communication & Notification System. This process can also be utilized to edit presence determination configurations already stored in the database.

At F8a, the Electronic Identification, Location Tracking, Communication & Notification System queries the Electronic Identification, Location Tracking, Communication & Notification Database for a list of available locations. Available locations can be ones that are entered into the system database as described in FIG. 2. Configuring refers to setting parameters for a location to assign a beacon or beacon cluster to a particular location as well as to aid in the determination of presence at that location based on signal strength and duration. This function can be typically reserved for a system administrator, though such is not considered limiting.

At F8b, the Electronic Identification, Location Tracking, Communication & Notification System displays a listing of available locations to configure. The system administrator or other authorized individual can then select the location to configure or edit the configuration of. Reconfiguring the location can be for a variety of reasons, such as, but not limited to, adding additional beacons to a location cluster for better accuracy, replace a beacon that is faulty, or changing the presence determination criteria to make the system more or less sensitive/accurate.

At F8c, once the location is selected, the system administrator may now specify the number of beacons assigned to this particular location. A location can consist of one or more beacons, clustered together.

Figure 17:
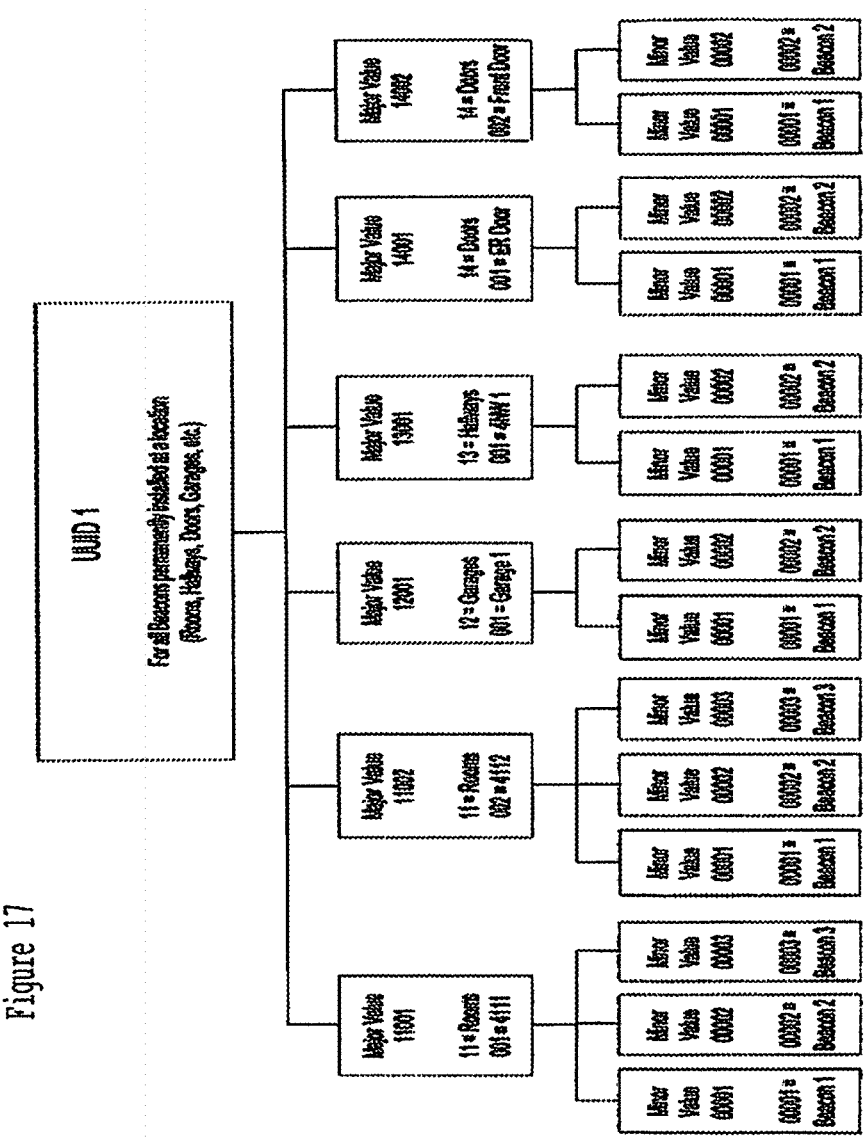
FIG. 17 is a block diagram of a non-limiting example for a beacon structure for a hospital using fixed location beacons.
Figure 18:
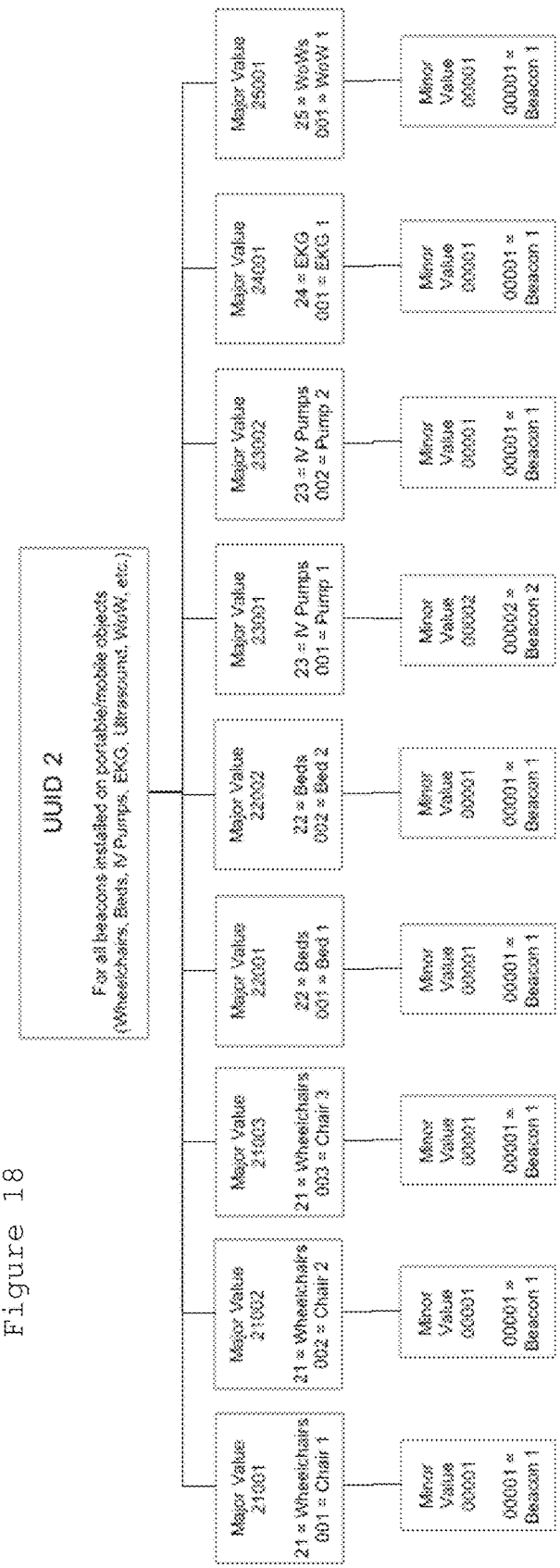
FIG. 18 is a block diagram of a non-limiting example for a beacon structure for a hospital using mobile asset tags.

Next, at F8d, the system administrator may now specify the Unique Identifiers for the beacons to be identified with this location. As a non-limiting example, if three beacons are configured for this location cluster, then 3 beacon identifiers must be selected to belong to this location cluster. If only a single beacon is selected then a single unique identifier is assigned to the particular location. Location can be identified by using matching identifiers on the beacons with only a single differentiator. In one embodiment, 3 identifying fields can be used for each beacon, UUID, Major Value and Minor Value. Each beacon can have values assigned to each of those 3 fields. As a non-limiting example, a 3 beacon cluster could have each beacon with a UUID of 121324-34235-342345-34423 and a major id value of 12345. Then beacon 1 in the cluster would have a minor value of 1, beacon 2 would have a minor value of 2 and beacon 3 would have a minor value of 3 (or some other differing numbering, lettering, characters or other indicia). The next cluster could have 3 beacons with the same UUID as above but with a different major value. See FIG. 17 as a non-limiting example for configuring beacons.

Next, at F8e, the system administrator may now select what the system should do when it does not receive a signal from a beacon assigned to a given location cluster. Non-limiting options include, but are not limited to, discarding this location from the presence determination if a signal from all beacons configured for the cluster is not received, assigning a default or static value for the beacon signal strength for any beacon that is assigned to the particular cluster but didn't receive a signal, or ignoring the beacon from consideration in the presence determination.

Next, at F8f, the system administrator may specify the Unique Identifiers for minimum signal strength threshold for a customer to be considered present at this particular location. This signal strength is the measure of the strength of a known wireless radio, sound and/or light-based beacons transmitted signal strength as received by the customer's electronic system or device or vice-versa for the embodiments that the customer's electronic device contains a beacon that transmits a signal and the wireless radio, sound and/or light-based beacons are provided with receivers for receiving the transmitted beacon signal sent from the customer's electronic device. As a non-limiting example, the signal strength can be measured and calculated on a scale of 0 to 100% where the minimum signal strength threshold is set to 80%. This means that unless the customer's device receives a signal from the wireless radio, sound and/or light-based beacons greater then the 80% strength threshold, they will not be considered present at a location (or vice versa where the customer's device sends a beacon signal and the cluster of beacons contain received for receiving the beacon signal of the customer's device). Though it is preferred that the beacons are of the same type for a particular cluster, it is within the scope of the disclosure to have a location cluster made up beacons of differing types (i.e. Bluetooth beacon, a light-based beacon and a sound based beacon). The signal strength measurement is intended to approximate the distance between the customer's electronic system or device and the wireless radio, sound and/or light-based beacons and can also include strength indicators including but not limited to RSSI (relative signal strength indicator) values. As mentioned above, RSSI is a signal strength indicator based on an industry standard algorithm that factors into account the known signal transmission power level.

At F8g, once the minimum presence signal strength threshold has been entered, the system administrator has the option of specifying the minimum presence duration for that location. The minimum presence duration is a time value and can be expressed in any known and acceptable time format including but not limited to milliseconds, seconds, minutes and hours. As a non-limiting example, the system administrator can configure the value to 20 seconds. In this instance the customer's electronic system or device must report to the Electronic Identification, Location Tracking, Communication & Notification system a signal strength above the minimum threshold specified in F8c for a period of at least 20 consecutive seconds in order to consider the customer's electronic system or device present at that location.

At F8h, the location's presence determination configuration profile is updated in the Electronic Identification, Location Tracking, Communication & Notification Database.

FIG. 9 demonstrates how a customer is able to order goods and/or services from within the Electronic Identification, Location Tracking, Communication & Notification Application on their electronic system or device.

At F9a, the customer opens the App on their electronic system or device and selects the order Goods/Services button, option or link. The App displays all available Goods and/or Service types available for the facility. The customer selects the type of good(s) and/or service(s) desired.

At F9b, the App then displays a menu of available goods and/or services for purchase in that category to the customer. The customer can select a single good or service, select multiple goods and/or services, enter in a free text request, initiate an audio or video session with a facility staff member, and/or use any other available method to select the goods and/or services desired.

At F9c, the customer's order is electronically transmitted to the Electronic Identification, Location Tracking, Communication & Notification System.

At F9d, the Electronic Identification, Location Tracking, Communication & Notification System queries the Electronic Identification, Location Tracking, Communication & Notification Database for the notification method associated with this category or good and/or service.

At F9e, the Electronic Identification, Location Tracking, Communication & Notification System notifies the appropriate person or department for the category of goods and/or services ordered by the customer of the order and any information provided by the customer.

FIG. 10 demonstrates how a facility is able to deliver goods and/or services ordered by a customer from within the Electronic Identification, Location Tracking, Communication & Notification Application on the customer's electronic system or device to the current location of the customer at the time of delivery.

At F10a, a facility staff member uses an electronic system or device to access the Electronic Identification, Location Tracking, Communication & Notification System at the time the good(s) and/or service(s) is (are) ready to be delivered to the customer.

At F10b, the Electronic Identification, Location Tracking, Communication & Notification System queries the Electronic Identification, Location Tracking, Communication & Notification Database for the current location of the customer who placed the order. The current location is determined as in FIGS. 3 and/or 4 and is constantly being updated within the Electronic Identification, Location Tracking, Communication & Notification System.

At F10c, the Electronic Identification, Location Tracking, Communication & Notification System then returns the current location of the customer to the Facility staff member's electronic system or device. In the event the customer moves from the location provided to the facility member's device, an alert or updated location information for the customer can be automatically transmitted to the facility staff member's device so that the staff member is provided with the new location for the customer.

FIG. 11 demonstrates how a customer is able to opt-out of being rated/monitored from within the Electronic Identification, Location Tracking, Communication & Notification Application on the customer's electronic system or device.

At F11a, when the Electronic Identification, Location Tracking, Communication & Notification System makes a determination that a customer's electronic system or device is present at a given location as described in FIGS. 3 and/or 4, a notification can be sent to the customer's electronic system or device via the Electronic Identification, Location Tracking, Communication & Notification Application "App" indicating the that their presence has been detected at a given location by the Electronic Identification, Location Tracking, Communication & Notification System. The notification can be made through a variety of methods including but not limited to Email, SMS, MMS, On Screen and Voice.

At F11b, the customer through the App running on their electronic system or device is presented with or can select a menu item to opt-out of being rated/monitored/tracked by the facility. If the customer does not make an affirmative selection to opt-out of being rated/monitored/tracked or makes an affirmative selection to allow rating/monitoring/tracking then the Electronic Identification, Location Tracking, Communication & Notification System can be electronically notified so that customer rating/monitoring/tracking can continue. Alternatively, the system can be programmed for the opposite scenario, such that an affirmative selection must be entered in order to opt-in to being rated/monitored/tracked.

At F11c, if the customer makes an affirmative selection to Opt-Out of being rated/monitored/tracked (or Opt-In in the alternative scenario), then the Electronic Identification, Location Tracking, Communication & Notification System is electronically notified of such selection.

At F11d, the Electronic Identification, Location Tracking, Communication & Notification System updates the Electronic Identification, Location Tracking, Communication & Notification Database of the customers' selection in F11b or F11c.

At F11e, for those customers who made the affirmative selection to Opt-Out of being monitored, the Electronic Identification, Location Tracking, Communication & Notification System queries the Electronic Identification, Location Tracking, Communication & Notification Database to determine if the customer is a member of the Opt-Out Group or List as configured in FIG. 5 for that customer and if so, what the notification settings are for the given customer.

At F11f, for customers determined to be part of the Opt-Out group or list, a notification is sent via the method configured for the customer and group type in FIG. 5.

FIG. 12 demonstrates one non-limiting embodiment of how a cluster of beacons can be assigned to a location and used for location determination within the Electronic Identification, Location Tracking, Communication & Notification System.

At F12a, beacons are installed and configured for four locations, Table A, Table B, Table C and Table D. Each table has 3 beacons configured in the cluster. It should be recognized that a table is just one of many non-limiting examples of where the beacons are located or associated with. Other non-limiting examples of beacon locations are rooms, booths, halls, doorways and even specific areas within a room.

At F12b, a customer with the Electronic Identification, Location Tracking, Communication & Notification Application on the customers' electronic system or device sits down at Table A as illustrated or otherwise positions him or herself at Table A.

At F12c, the Electronic Identification, Location Tracking, Communication & Notification Application on the customers' electronic system or device receives beacon signals from all nearby beacons and sends them to the Electronic Identification, Location Tracking, Communication & Notification System. As a non-limiting example, the signal strength measurements for each beacon is displayed in the chart on the figure. The Electronic Identification, Location Tracking, Communication & Notification System calculated a signal average for each location based on all of the beacon signal strengths received.

At F12d, the Electronic Identification, Location Tracking, Communication & Notification System makes a determination on presence at the location of Table A based on a higher average signal strength received from the beacons in the Table A location cluster then the average signal strength received from the beacons in the other location clusters. Preferably, the system continuously monitors for the customer's location. However, it is within the scope of the disclosure to provide for a configurable setting for how frequently the system checks for beacons, which can be, without limitation, anywhere from about every second to about every 30 seconds. Periodic checking, as opposed to continuous monitoring, would provide for lower battery usage on the phone/electronic device.

Certain embodiments the one or more beacons transmit their respective signals for receipt by a receiver within the customer/end user's electronic device. For the embodiments described above where the wireless signal is sent by customer/end user's electronic device and received by one or more beacons located in the premises, the customer's electronic device also has or acts as a beacon (transmits a wireless signal) and each of the one or more beacons located on the premises is provided with its own receiver for receiving the signal from the electronic device. Where the customer's electronic device acts as receiver, the App can be used to filter or disregard received signals that are below the preconfigured signal strength threshold and/or are not above the preconfigured signal strength threshold for the preconfigured duration of time. In this situation, the App can be programmed only to electronically send information to the Electronic Identification, Location Tracking, Communication & Notification System ("System") for the signals satisfying the preconfigured signal strength threshold or the preconfigured signal strength threshold and preconfigured duration of time. Where the customer's electronic device transmits the signal to the plurality of beacons located on the premises, the beacons preferably electronically send all of the information to the System and any filtering or disregarding of any of the signals is determined by the System and not prior to being sent to the System.

The system that performs the above described functions and steps can include several components including, but not necessarily limited to, the following:
1. One or more Wireless Radio, Sound and/or Light-based Beacon(s)
2. One or more customer electronic computer system or device(s)
3. Electronic Identification, Location Tracking, Communication & Notification System
4. Electronic Identification, Location Tracking, Communication & Notification Database
5. A public or private computer network to connect or communicate the customer's device, beacons and Electronic Identification, Location Tracking, Communication & Notification system and database with each other.

The various components can be in electrical and wireless communication with each other.

As one non-limiting example, the ability to electronically identify customers, track customer movements and notify providers of hospitality services of the presence of desired customers will provide significant administrative and financial benefits incident to operators of hospitality venues. Without limitation, these include the following benefits:

1. Provide hospitality service providers the ability to identify a customer and the customer's precise location within their facility.
2. Provide customers with real-time mapping and navigation in buildings and hospitality venues.
3. Provide hospitality service providers the ability to receive notifications when selected customers are present in their facility.
4. Analyze customer levels and behavior so as to tailor or modify service offerings and maximize profitability.

It should be understood that the exemplary embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from their spirit and scope.

All components of the described system and their locations, electronic communication methods between the system components, electronic storage mechanisms, etc. discussed above or shown in the drawings, if any, are merely by way of example and are not considered limiting and other component(s) and their locations, electronic communication methods, electronic storage mechanisms, etc. can be chosen and used and all are considered within the scope of the disclosure.

Unless feature(s), part(s), component(s), characteristic(s) or function(s) described in the specification or shown in the drawings for a claim element, claim step or claim term specifically appear in the claim with the claim element, claim step or claim term, then the inventor does not consider such feature(s), part(s), component(s), characteristic(s) or function(s) to be included for the claim element, claim step or claim term in the claim when and if the claim element, claim step or claim term is interpreted or construed. Similarly, with respect to any "means for" elements in the claims, the inventor considers such language to require only the minimal amount of features, components, steps, or parts from the specification to achieve the function of the "means for" language and not all of the features, components, steps or parts describe in the specification that are related to the function of the "means for" language.

The benefits, advantages, solutions to problems, and any element(s) that may cause any benefit, advantage, or solution to occur or become more pronounced are not to be construed or considered as a critical, required, or essential features or elements of any or all the claims.

While the disclosure has been described and disclosed in certain terms and has disclosed certain embodiments or modifications, persons skilled in the art who have acquainted themselves with the disclosure, will appreciate that it is not necessarily limited by such terms, nor to the specific embodiments and modification disclosed herein. Thus, a wide variety of alternatives, suggested by the teachings herein, can be practiced without departing from the spirit of the disclosure, and rights to such alternatives are particularly reserved and considered within the scope of the disclosure.

What is claimed is:

1. A method for determining a current location of an individual at a particular geographical area, said method comprising the steps of:
   a. receiving one or more wireless signals by an electronic device on the possession of the individual sent by a plurality of wireless beacons with subsets of the plurality of wireless beacons grouped together to form a particular beacon cluster of a plurality of beacon clusters with each particular beacon cluster associated with a particular location in the particular geographic area, said electronic device having and running an electronic identification, location tracking, communication and notification app ("App"), each wireless signal of the one or more wireless signals associated with a specific one beacon from the one or more wireless beacons, each of the signals of the one or more wireless signals having an unique identifier identifying the specific one beacon from the one or more wireless beacons that the signal was transmitted from, each of the one or more beacons located at a different spot within the particular geographical area; and b. electronically forwarding at least some of the one or more wireless signals by the electronic device to an electronic identification, location tracking, communication and notification system ("System") to determine the current location of the individual at the particular geographical area; and c. obtaining an average signal strength value for a beacon cluster by (i) averaging signal strengths for the received signals for all of the beacons in the beacon cluster, (ii) assigning a dummy value for signal strengths below the preconfigured signal strength threshold sent from a beacon in the beacon cluster and then averaging all signal strengths above the threshold and the dummy value assigned, or (iii) averaging only signal strengths above the preconfigured signal strength threshold from beacons in the beacon cluster.

2. The method for determining of claim 1 further comprising the steps of determining by the App running on the individual's electronic device the signal strength for each of the received wireless signals and electronically forwarding only signals having signal strengths above a preconfigured signal strength threshold.

3. The method for determining of claim 2 wherein the received signals having a signal strength over the preconfigured threshold are only electronically forwarded by the App to the System only where the signal strength remains above the preconfigured signal strength threshold for a preconfigured duration of time.

4. The method for determining of claim 1 further comprising the step of querying an electronic identification, location tracking, communication and notification database (Database") by the System and receiving configuring information by the System from the Database for each of the beacons from the plurality of wireless beacons.

5. The method for determining of claim 4 wherein the configuring information including minimum signal strength thresholds for the wireless signal transmitted by each beacon in order for the beacon to be considered in a determination for a current location of the individual.

6. The method for determining of claim 5 further comprising the step of disregarding wireless signals received by the individual's electronic device having a signal strength that are below the minimum signal strength threshold for their associated beacon.

7. The method for determining of claim 6 further comprising the step of determining the current location for the individual within the particular geographic area by the System using only wireless signals received by the individual's electronic device having signal strengths above the minimum signal strength threshold.

8. The method for determining of claim 1 wherein the particular geographical area is a hospitality location.

9. The method for determining of claim 8 wherein the hospitality location is a casino or a hotel.

10. The method for determining of claim 8 further comprising the step of electronically sending notification to an electronic device of a staff member employed at the hospitality location regarding a presence and a current location of the individual within the hospitality location.

11. The method for determining of claim 1 further comprising the steps of identifying the received wireless signal with a highest signal strength from the received plurality of wireless signals, obtaining location information for the associated beacon which sent the signal with the highest signal strength from an electronic identification, location tracking, communication and notification database ("Database") and selecting the location of the beacon which sent the wireless signal with the highest signal strength as a current location for the individual within the particular geographical area.

12. The method for determining of claim 1 wherein each beacon cluster containing beacons not in any of the other beacon clusters and obtaining an average signal strength value for each beacon cluster based on the beacons contained in each cluster.

13. The method for determining of claim 12 wherein each beacon cluster defining a specific location within the particular geographic area and the beacon cluster having the highest average signal strength identifies the specific location of the individual within the particular geographic area.

14. A method for determining a current location of an individual at a particular geographical area, said method comprising the steps of:

a. receiving one or more wireless signals by an electronic device on the possession of the individual sent by one or more wireless beacons, said electronic device having and running an electronic identification, location tracking, communication and notification app ("App"), each wireless signal of the one or more wireless signals associated with a specific one beacon from the one or more wireless beacons, each of the signals of the one or more wireless signals having an unique identifier identifying the specific one beacon from the one or more wireless beacons that the signal was transmitted from, each of the one or more beacons located at a different spot within the particular geographical area;

b. electronically forwarding at least some of the one or more wireless signals by the electronic device to an electronic identification, location tracking, communication and notification system ("System") to determine the current location of the individual at the particular geographical area; and c. determining by the App running on the individual's electronic device the signal strength for each of the received wireless signals and electronically forwarding only signals having signal strengths above a preconfigured signal strength threshold;

wherein the one or more beacons are a plurality of beacons and further comprising the steps of grouping two or more of the plurality of beacons into a plurality of beacon clusters, with each beacon cluster containing beacons not in any of the other beacon clusters and obtaining an average signal strength value for each beacon cluster based on the beacons contained in each cluster;

wherein an average signal strength for a beacon cluster is determined by (i) averaging signal strengths for the received signals for all of the beacons in the beacon cluster, (ii) assigning a dummy value for signal strengths below the preconfigured signal strength threshold sent from a beacon in the beacon cluster and then averaging all signal strengths above the threshold and the dummy value assigned, or (iii) averaging only signal strengths above the preconfigured signal strength threshold from beacons in the beacon cluster.

15. A method for determining a current location of an individual at a particular geographical area, said method comprising the steps of:
   a. receiving a wireless signal sent from an electronic device on the possession of the individual by one or more wireless beacons, said electronic device having and running an electronic identification, location tracking, communication and notification app ("App"), each beacon of the one or more beacons having a receiver for receipt of the wireless signals, each of the one or more beacons located at a different spot within the particular geographical area;
   b. electronically forwarding a wireless signal by each beacon of the one or more beacons to an electronic identification, location tracking, communication and notification system ("System"), each wireless signal sent by the beacon to the System containing information identifying the individual assigned to the electronic device, a unique identifier for the beacon and the signal strength of the wireless signal received by the beacon from the electronic device to allow the System to determine the current location of the individual at the particular geographical area; and
   c. determining by the App running on the individual's electronic device the signal strength for each of the received wireless signals and electronically forwarding only signals having signal strengths above a preconfigured signal strength threshold wherein the received signals having a signal strength over the preconfigured threshold are only electronically forwarded by the App to the System only where the signal strength remains above the preconfigured signal strength threshold for a preconfigured duration of time; and
   d. obtaining an average signal strength value for a beacon cluster by (i) averaging signal strengths for the received signals that are electronically forwarded in step c. or (ii) assigning a dummy value for signals that were not electronically forwarded in step c. and then averaging all signal strengths of the electronically forwarded signals and the dummy value assigned.

16. The method for determining of claim 15 further comprising the step of querying an electronic identification, location tracking, communication and notification database (Database") by the System and receiving configuring information by the System from the Database for each of the beacons from the one or more wireless beacons.

17. The method for determining of claim 16 wherein the configuring information including minimum signal strength thresholds for the wireless signals received by each beacon from the electronic device in order for the beacon to be considered in a determination for a current location of the individual.

18. The method for determining of claim 17 further comprising the step of determining the current location for the individual within the particular geographic area by the System using only wireless signals received by the beacons having signal strengths above the minimum signal strength threshold.

19. The method for determining of claim 15 further comprising the steps of identifying the received wireless signal with a highest signal strength from the wireless signals received by the one or more beacons, obtaining location information for the beacon who received the sent the signal with the highest signal strength from an electronic identification, location tracking, communication and notification database ("Database") and selecting the location of the beacon which received the wireless signal with the highest signal strength as a current location for the individual within the particular geographical area.

20. The method for determining of claim 19 further comprising the step of electronically sending notification to an electronic device of a staff member employed at the particular geographical area regarding a presence and the current location of the individual within the particular geographical area.

* * * * *